(12) United States Patent
Izraelev (10) Patent No.: US 7,052,253 B2
(45) Date of Patent: *May 30, 2006

(54) SEAL AND BEARING-FREE FLUID PUMP INCORPORATING A PASSIVELY SUSPENDED SELF-POSITIONING IMPELLER

(75) Inventor: Valentin M. Izraelev, Eden Prairie, MN (US)

(73) Assignee: Advanced Bionics, Inc., Hopkins, MN (US)

( * ) Notice: Subject to any disclaimer, the term of this patent is extended or adjusted under 35 U.S.C. 154(b) by 313 days.

This patent is subject to a terminal disclaimer.

(21) Appl. No.: 10/440,578

(22) Filed: May 19, 2003

(65) Prior Publication Data

US 2004/0234391 A1    Nov. 25, 2004

(51) Int. Cl.
*F04B 17/00* (2006.01)
*H02K 7/09* (2006.01)

(52) U.S. Cl. ............... 417/423.12; 417/423.1; 310/90.5

(58) Field of Classification Search ........... 417/423.12, 417/423.13, 423.1, 410.1; 310/90.5
See application file for complete search history.

(56) References Cited

U.S. PATENT DOCUMENTS

| | | | |
|---|---|---|---|
| 2,319,730 A | 5/1943 | Garraway | |
| 3,433,163 A | 3/1969 | Sheets et al. | |
| 3,890,019 A | 6/1975 | Bodem et al. | |
| 3,938,913 A | 2/1976 | Isenberg et al. | |
| 3,957,389 A | 5/1976 | Rafferty et al. | |
| 3,970,408 A | 7/1976 | Rafferty et al. | |
| 4,036,565 A | 7/1977 | Becker | |
| 4,057,369 A | 11/1977 | Isenberg et al. | |
| 4,382,199 A * | 5/1983 | Isaacson | 310/87 |
| 4,688,998 A | 8/1987 | Olsen et al. | |
| 4,779,614 A | 10/1988 | Moise | |
| 4,944,748 A | 7/1990 | Bramm et al. | |
| 4,994,078 A | 2/1991 | Jarvik | |
| 4,995,857 A | 2/1991 | Arnold | |

(Continued)

FOREIGN PATENT DOCUMENTS

DE      2342767      3/1975

(Continued)

OTHER PUBLICATIONS

Olsen et al., "Blood Pump with a Magnetically Suspended Impeller", Trans. Am. Soc. Artif. Inter. Organs. vol. XXXL 1985, pp. 395-401.

(Continued)

*Primary Examiner*—Charles G. Freay
*Assistant Examiner*—Timothy P. Solak
(74) *Attorney, Agent, or Firm*—Haugen Law Firm PLLP (57) ABSTRACT

A novel fluid pump includes a stator body defining a pumping chamber and an impeller operationally disposed within the chamber. The impeller has opposed ends with a central axis defining an axis of rotation. Passive magnetic bearing sets are positioned along the impeller body with each bearing set being similarly polarized so as to be in mutually attracting or mutually repelling relationship. A third passive magnetic bearing set is positioned along the impeller axis between the opposed ends with the third bearing set being magnetically coupled similarly to the first and second bearing sets, with the passive magnetic bearings creating an unstable negative force in a plane perpendicular to the axis of rotation of the impeller with the negative stiffness being overcome upon rotation of the impeller creating a centrifugal force of a magnitude greater than that of the unstable negative force.

7 Claims, 6 Drawing Sheets

U.S. PATENT DOCUMENTS

| | | | |
|---|---|---|---|
| 5,049,134 | A | 9/1991 | Golding et al. |
| 5,055,005 | A | 10/1991 | Kletschka |
| 5,078,741 | A | 1/1992 | Bramm et al. |
| 5,112,200 | A | 5/1992 | Isaacson et al. |
| 5,158,440 | A | 10/1992 | Cooper et al. |
| 5,195,877 | A | 3/1993 | Kletschka |
| 5,205,721 | A | 4/1993 | Isaacson |
| 5,211,546 | A * | 5/1993 | Isaacson et al. ............ 417/356 |
| 5,326,344 | A | 7/1994 | Bramm et al. |
| 5,385,581 | A | 1/1995 | Bramm et al. |
| 5,470,208 | A * | 11/1995 | Kletschka .................. 417/356 |
| 5,685,700 | A | 11/1997 | Izraelev |
| 6,244,835 | B1 * | 6/2001 | Antaki et al. ............... 417/356 |
| 6,375,607 | B1 * | 4/2002 | Prem .......................... 600/17 |
| 6,861,778 | B1 * | 3/2005 | Izraelev .................... 310/90.5 |

FOREIGN PATENT DOCUMENTS

| | | |
|---|---|---|
| DE | 3130974 | 2/1983 |
| GB | 1359007 | 7/1974 |

OTHER PUBLICATIONS

Bramm et al., "The Sealless and Bearingless Rotor Blood Pump System: Adaptation . . . Thermal Heat Up" Assisted Circulation 3. F. Unger (Ed.). Springer-Verlag Berlin Heidelberg, 1989, pp. 215-224.

Ohara et al., "The Next Generation Baylor C-Gyro Pump: Anthithrombogenic 'Free Impeller' Design for Long-Term Centrifugal VAD". Artif. Organs. vol. 18, No. 3. 1994, pp. 238-243.

Treichler et al., "A Fluid Dynamic analysis of a Rotary Blood Pump for Design Improvement". Artificial Organs, vol. 17. No. 9, 1993. pp. 797-808.

* cited by examiner

SEAL AND BEARING-FREE FLUID PUMP INCORPORATING A PASSIVELY SUSPENDED SELF-POSITIONING IMPELLER

CROSS-REFERENCE TO RELATED APPLICATION

This application relates to my co-pending application Ser. No. 10/376,875, filed Feb. 28, 2003.

BACKGROUND OF THE INVENTION

The present invention relates generally to a novel suspension system for the rotor component in a rotor/stator assembly, and more particularly to such a system which provides for passive and stable suspension of the rotor within a fluid pump. Assemblies utilizing the features of the present invention are adapted for a wide variety of applications, including fluid handling systems for fragile or aggressive fluids, as well as applications for such assemblies which may be characterized as either delicate and/or rugged. The novel passive and stable suspension system of the present invention includes a rotor which is typically suspended within a stator, with the rotor being stabilized through passive magnetic as well as hydrodynamic forces.

The magnetic components may be designed in a variety of different coupling arrangements, with passive magnetic bearings being employed for creating stability along certain selected planes or axes and further creating one resultant unstable negative force in one plane or along an axis. More specifically, the magnetic forces are designed to create an unstable negative force in a plane perpendicular to the axis of rotation of the rotor, with stable and positive forces and moments being created in all other degrees of freedom excepting of course, rotation of the rotor. This resultant instability in the plane perpendicular to the axis of rotation is overcome upon rotation of the rotor creating a centrifugal force of magnitude greater than that of the unstable negative force. In other words, when rotating, the forces created in the rotor return the body to an appropriate point of origin for the intersection of the X, Y and Z axes. Here, the positive forces and moments are defined as forces and moments applied to the rotor in the direction of the origin, and, correspondingly, negative forces and moments apply to the rotor in directions away from the origin.

The suspension system of the present invention utilizes magnetic bearings for creation of positive stiffness and a resultant negative stiffness, with the overall stiffness in five of the six degrees of freedom being positive. Dynamic stability of the system is ultimately achieved through centrifugal/centripital forces, with dynamic stability being achieved.

Except for the passive magnetic stabilization system and the dynamic magnetic forces utilized to drive the rotor, the fluid pumps of the present invention are otherwise bearing and seal-free. Passive magnetic forces are applied to the rotor during periods of rotation and dwell, with these passive forces including a resultant unstable negative force in a plane or along an axis perpendicular to the axis of rotation. As such, fluid pumps employing the magnetically stabilized rotor/stator assemblies of the present invention are particularly well adapted for a wide variety of mechanical applications, with one such application being in a centrifugal pump for handling highly aggressive materials such as corrosive, poisonous, or dangerously radioactive fluids, as well as fragile fluids including human or animal blood.

Another pump application is an axial pump. The impeller in centrifugal pumps transfers the kinetic energy to the fluid by blades/vanes disposed thereon, or by surfaces based on Tesla principles. Such surfaces may include, for example, parallel or non-parallel disks or cones radially arranged about and extending from the rotor axis. During any transfer/movement of such fluids, it is frequently dangerous to expose the fluids to forces such as unusual impact and/or shear forces, and thus the advantage of utilizing bearing and seal-free pumps, and particularly one wherein the rotor/stator assembly is at least partially magnetically stabilized.

A particularly advantageous feature of the present invention is that of providing a passive magnetic force to the rotor which when combined with centrifugal forces created in rotation of the rotor in fluid, reduces and/or completely eliminates surface-to-surface contact between rotor and stator surfaces. Elimination of the surface-to-surface contact between the rotor and stator prevents undesired frictional heat input, as well as premature wearing of the respective components of the fluid pump. An additional aspect of the passive magnetic suspension combined with such centrifugal forces is in the fact that the clearance between the rotor and the stator is not a critical dimension with respect to the maintenance of a properly suspended rotor within the stator. Therefore, fluid pumps having relatively larger clearances between the rotor and stator are made possible by the suspension system of the present invention. Such larger clearances accordingly reduce shear forces that can be damaging to fragile fluids. In fact, the clearances between the rotor and the housing in fluid pumps of the present invention are sufficiently large so as to negate boundary layer pressure effects and fluid shear stresses under the Prandl theory that are commonly referred to as "hydrodynamic bearings". Accordingly, rotors utilized in the present invention do not rely upon such hydrodynamic bearings to remain properly positioned within the pump housing, but rather are positionably stabilized through the combination of passive magnetic bearings and centrifugal forces generated in operable rotation of the rotor.

In connection with one application of the present invention, pump assemblies utilizing the features of the present invention may be exposed to aggressive fluids, including corrosive, poisonous or radioactive fluids, as well as fluids which cannot tolerate contamination. Through elimination of seals and/or bearings, the lifetime and/or longevity of the pump is substantially increased.

Poisonous fluids, for example, become extremely dangerous whenever leakage develops, a common consequence of bearing and seal failure. In fluid pumps in accordance with the present invention, a rotor or impeller is utilized in an assembly which is bearing and seal-free, with the rotor being dynamically balanced and stable during operation. Bearing and seal-free pumps utilizing the rotor/stator assemblies of the present invention are particularly well adapted for transferring human blood and other delicate liquids without damaging and/or otherwise significantly adversely affecting their composition or quality. Furthermore, the magnetic stabilization feature of the present invention provides stable positioning of the rotor during operation. The passively suspended rotor is preferably operably positioned within the stator independent of forces external to the fluid pump. Depending upon the application, the rotor may be fabricated from any of a variety of non-magnetic materials, including, for example, metals such as titanium and non-metals such as pyrolytic carbon. Certain engineered plastics have also been found useful.

Another feature of rotors and stators suitable for application in the present invention is that they be capable of receiving and reliably retaining passive magnetic components which deliver forces stabilizing the rotor. Although not in the form of a mechanical surface-contacting bearing, the passive magnetic components utilized in the present invention may be positioned and/or arranged to function as magnetic thrust bearings. The rotor is also arranged to be capable of receiving and reliably retaining magnetic components such as electromagnetic components used in the drive system for delivering energy to the rotor for rotation. Preferably, an array of permanent magnets are positioned within the rotor and stator components in a brushless motor configuration. Alternatively, the drive mechanism may employ permanent magnet-to-permanent magnet couplings similarly mounted. The arrangement of the present invention provides for the economic utilization of a magnetically levitated rotor/stator assembly which may be fabricated by conventional processes, and therefore highly economically viable. Rotor stabilization and/or suspension may be achieved with passive magnetic bearings such as positioned in different arrangements or configurations. In preferred configurations, magnetically coupled bearings may provide positive forces in five of the six possible degrees of freedom, while providing one unstable negative force, preferably in a plane perpendicular to the axis of rotation, with this instability being overcome by a centrifugal force of greater magnitude.

GENERAL COMMENTARY

An English scientist, Rev. Samuel Earnshaw concluded in his paper published in 1839 that it is impossible to create a passive stable suspension of a body using passive electromagnetic and electrostatic forces. Following Earnshaw's theory and utilizing stable suspension or levitation, active magnetic bearings including permanent magnets and coils have been utilized to control and/or manipulate one or more degrees of freedom. Alternatively, superconductors may be utilized instead of magnetic bearings, however means for achieving a result appear impractical. Active magnetic bearing technology functions, but it has been found complex, costly, and less reliable than other mechanical means. In certain applications, active magnetic bearings are substituted by a combination of hydrodynamic and mechanical journal bearings, but in such cases, it is not a true suspension since clearances between the rotor and the journal are tight, frequently in the range of between 4 and 12 microns, although slightly greater tolerance levels may be satisfactorily utilized in certain applications.

When an object such as a rotor rotates in a liquid fluid medium, the rotor and the medium interact and inertial centrifugal/centripital forces are created. These forces are governed by the following equation:

$$F_c = \Delta\rho(W^2)(R_c)(V)$$

wherein:
$F_c$=centrifugal force acting on the rotor in the direction perpendicular to the axis of rotation;
$\Delta\rho$=density of fluid−density of rotor;
W=angular velocity of excursion of the rotor axis of rotation;
$R_c$=radius of excursion of the rotor axis of rotation; and
V=volume of the rotor.

When the density of the rotor is less than that of the fluid medium, the resultant inertial force $F_c$ acting on the rotor is directed toward the axis of rotation and is a source of creation of positive stiffness for rotor suspension in two degrees of freedom perpendicular to the axis of rotation. For the rotor 12 in FIG. 1, these two degrees of freedom are displacements in the X and Y directions.

In certain applications, the passive and stable suspension of the rotor may be achieved by utilizing the hydrodynamic and inertial forces developed in rotation of the rotor in the fluid. Since the centrifugal force $F_c$ is dependent upon the square of the rate of rotation, stable passive levitation is achieved only after reaching a predetermined level of rate of rotation.

In other applications, the operational effect of a relatively low density rotor may be used in combination with non-contact bearings, namely passive magnetic bearings, to further stabilize and suspend the rotor within the pump. In these instances, the positive stiffness created by centrifugal forces becomes greater than the resultant negative stiffness of the passive permanent magnet system created in the same plane. In such a manner, stable suspension of the rotor may be achieved. Thus, the centrifugal forces developed in operation of the fluid pump of the present invention overpower those forces of instability considered by Earnshaw in his conclusion.

In the present arrangement, it will be appreciated that passive and stable suspension of the rotor may be obtained with the rotor being of a selected density less than the density of the medium in which it rotates. This passive and stable suspension is achieved with permanent magnet pairs configured to provide permanent magnetic bearings, and with the rotor having its selected density less than that of the medium in which it is rotated. In each instance, the rotor is driven by non-contact means, such as a magnetic assembly in a brushless motor configuration.

In the present arrangement, centrifugal/centripital forces developed through rotor rotation in combination with passive magnetic forces overcome any instability in the X, Y and Z axes. The ratios of positive and any resultant negative stiffness of magnetic bearings are such that overall positive stiffness of the rotor assembly is achieved through all five degrees of rotor freedom aided by centrifugal/centripital forces developed in the rotating fluid/medium. The rotor is therefore rendered stably suspended in the medium when the restoring forces from positive stiffnesses of the system in the respective degrees of freedom are greater than external destabilizing forces of negative stiffness.

SUMMARY OF THE INVENTION

Therefore, it is a primary object of the present invention to provide a fluid pump incorporating a passive and stable suspension of a rotor utilizing magnetic or electrostatic forces applied relative to a reference frame.

It is a further object of the present invention to provide a stable suspension of a rotor within a fluid pump with positive stiffness in all five degrees of freedom, excepting in the sixth degree of freedom which is defined as rotation around or about the axis of rotation of the rotor when a torque is applied.

It is a further object of the present invention to provide a passive and stable suspension of a rotor within a fluid pump utilizing inertial dynamic interaction between the rotor and a fluid medium in which the rotor rotates to create positive stiffness in all five degrees of freedom of the rotor.

Yet a further object of the present invention is to provide a passive and stable suspension of the rotor incorporating passive permanent magnetic bearings and dynamic interaction between the rotor and a fluid medium in which the rotor is rotating for use in a fluid pump.

It is a further object of the present invention to provide a novel passive and stably suspended rotor in a one of a kind mechanism employing a rotor confined within a stator, and wherein stability is achieved through rotation of the rotor.

It is yet a further object of the present invention to provide a novel rotor/stator assembly in a fluid pump wherein the rotor is disposed within the core of the stator, creating an annular zone between the chamber walls and the rotor surface, and wherein a fluid media fill is provided in the annular zone, and with forces being exerted or applied to the fluid media upon rotation of the rotor.

It is yet a further object of the present invention to provide a novel rotor/stator assembly wherein a fluid media flows into and out of the stator chamber.

Other and further objects of the present invention will become apparent to those skilled in the art upon a study of the following specification, appended claims, and accompanying drawings.

DESCRIPTION OF THE PREFERRED EMBODIMENTS

Figure 1:
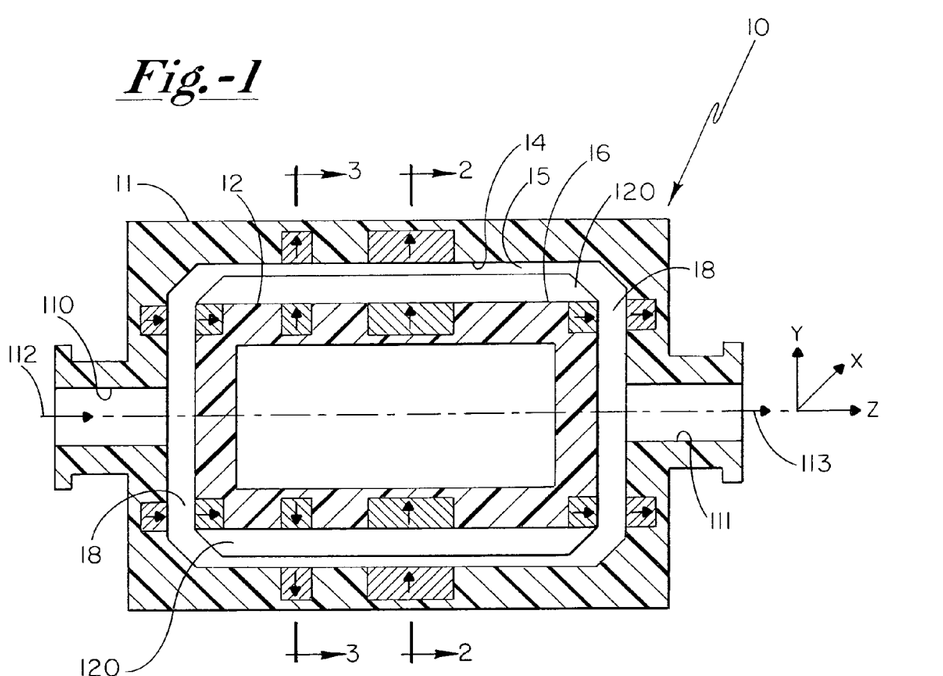
FIG. 1 is a sectional view taken through the diameter of a rotor/stator assembly in an axial pump embodiment and with portions of the stator being removed with polarity of the magnetic components being demonstratively indicated with arrows.
Figure 2:
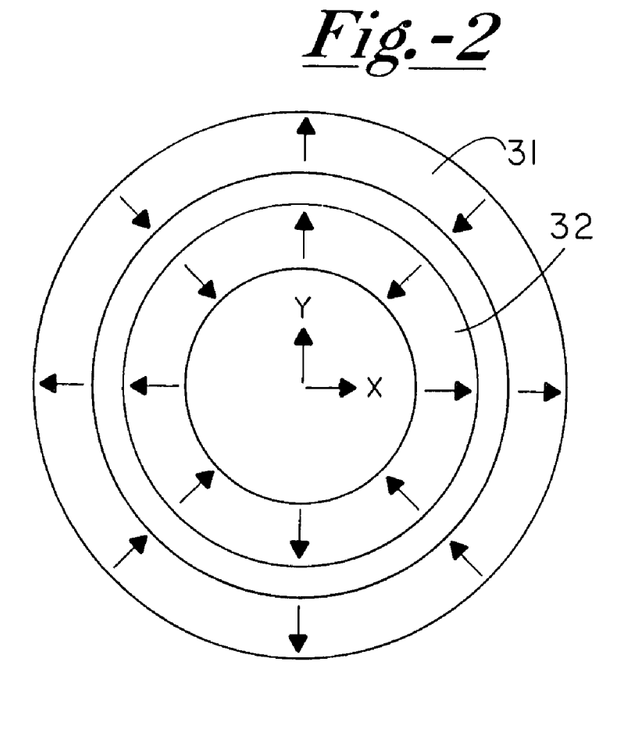
FIG. 2 is a view taken along the line and in the direction of the arrows 2—2 of FIG. 1 and illustrating one embodiment of a magnetic drive coupling arrangement, and with the polarity of the magnets being dynamically altered by electromagnetic means for creating relative rotation between rotor and stator.

With reference to the device illustrated in FIG. 1, the pump generally designated 10 comprises a shell or housing 11 along with a rotor structure 12. Housing 11 has an inner wall 14 which defines the chamber zone 15 therewithin. Rotor 12 has an outer surface as at 16 which is spaced from wall 14, thereby configuring chamber zone 15 into an annular zone. End zone openings 18—18 are provided which comprise faces or bases. The zones 15 and 18—18 are normally filled with media or fluid as indicated in FIG. 1. Housing 11 includes fluid inlet 110 and fluid outlet 111.

Preferably, rotor 12 includes a plurality of blades or vanes 120 disposed longitudinally along outer surface 16 thereof. Fluid inflow, as indicated by arrow 112, is directed into end zones 18—18 and chamber zone 15, and is drawn therethrough by rotational movement of rotor 12 and blades/vanes 120. Accordingly, the fluid is driven out from pump 10 through outlet 111, as indicated by arrow 113.

Rotor 12 has six degrees of freedom in a Cartesian coordinate system, these degrees of freedom being manifested in forces delivered along coordinate axes and rotation about these axes.

The origin of the system is located in the geometrical center of the rotor 12. In rotor 12, one degree of freedom is preserved for rotation about the Z axis. Support of rotor 12 is provided, with the support having the positive stiffness in each of the other five degrees of freedom, with "positive stiffness" being defined as a restoring force created whenever displacement from the origin occurs. In other words, the restoring force created by centrifugal forces return the body to the origin, thus providing overall stability for the operational structure. "Negative stiffness", on the other hand, is a force moving or rotating the body from the origin. Applying this conclusion to the present circumstance, and using as an example, rotor 12, it would be concluded that rotor 12 cannot be stably suspended by applying only permanent (passive) magnets for all required degrees of freedom.

Figure 3:
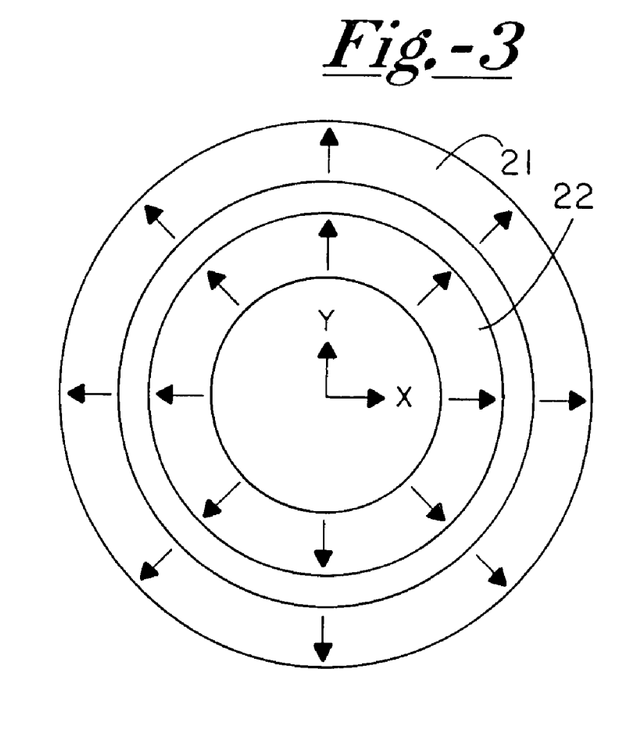
FIG. 3 is a view taken along the line and in the direction of the arrows 3—3 of FIG. 1 and illustrating an alternative embodiment of the relative arrangement of polarity of the magnetic bearing coupling.
Figure 5:
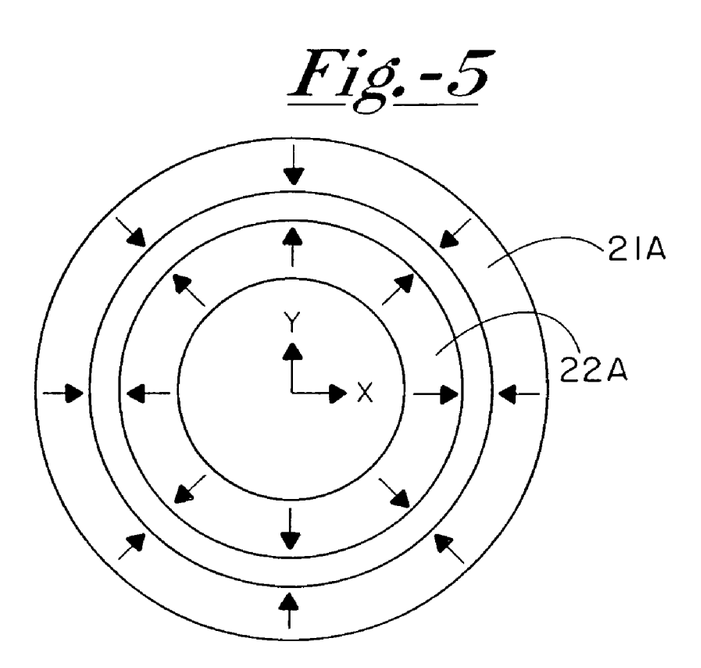
FIG. 5 is a view similar to FIG. 3 and illustrating an alternative magnetic bearing coupling arrangement utilizing modified arrangement of polarity, with this arrangement of polarity not being incorporated into the embodiment of FIGS. 1–4.

Depending upon the respective magnetization polarities of the passive magnet pairs 21 and 22 comprising a magnetic bearing for mounting in the stator and rotor, attractive or repulsive forces from permanent magnets comprising the bearing can be obtained. These are illustrated in FIGS. 3 and 5 respectively. Magnetization polarities, orientations, or directions are represented by arrows, with the attractive bearing in FIG. 3 being stable along the Z axis and unstable along X and Y axes. The magnetically repulsive bearing illustrated in FIG. 5 and comprising magnetic pairs 21A and 22A is stable in the direction of the X and Y axes, and unstable in the Z axis. In addition to those forces created from the axially spaced permanent magnetic bearing pairs, additional stabilizing and destabilizing forces are created by the magnetic drive coupling utilized to cause relative rotation between rotor and stator components. Stated another way, when attractive forces are involved in the permanent magnet arrangement of FIG. 3, the system becomes stable in the axis of rotation, and when repulsive forces are utilized as in FIG. 5, then the system becomes unstable in the axis of rotation. In this connection, the numerical designations for components in FIG. 5 are identified with the suffix "a", and except for polarity, are the same as those components of FIG. 3.

Figure 4:
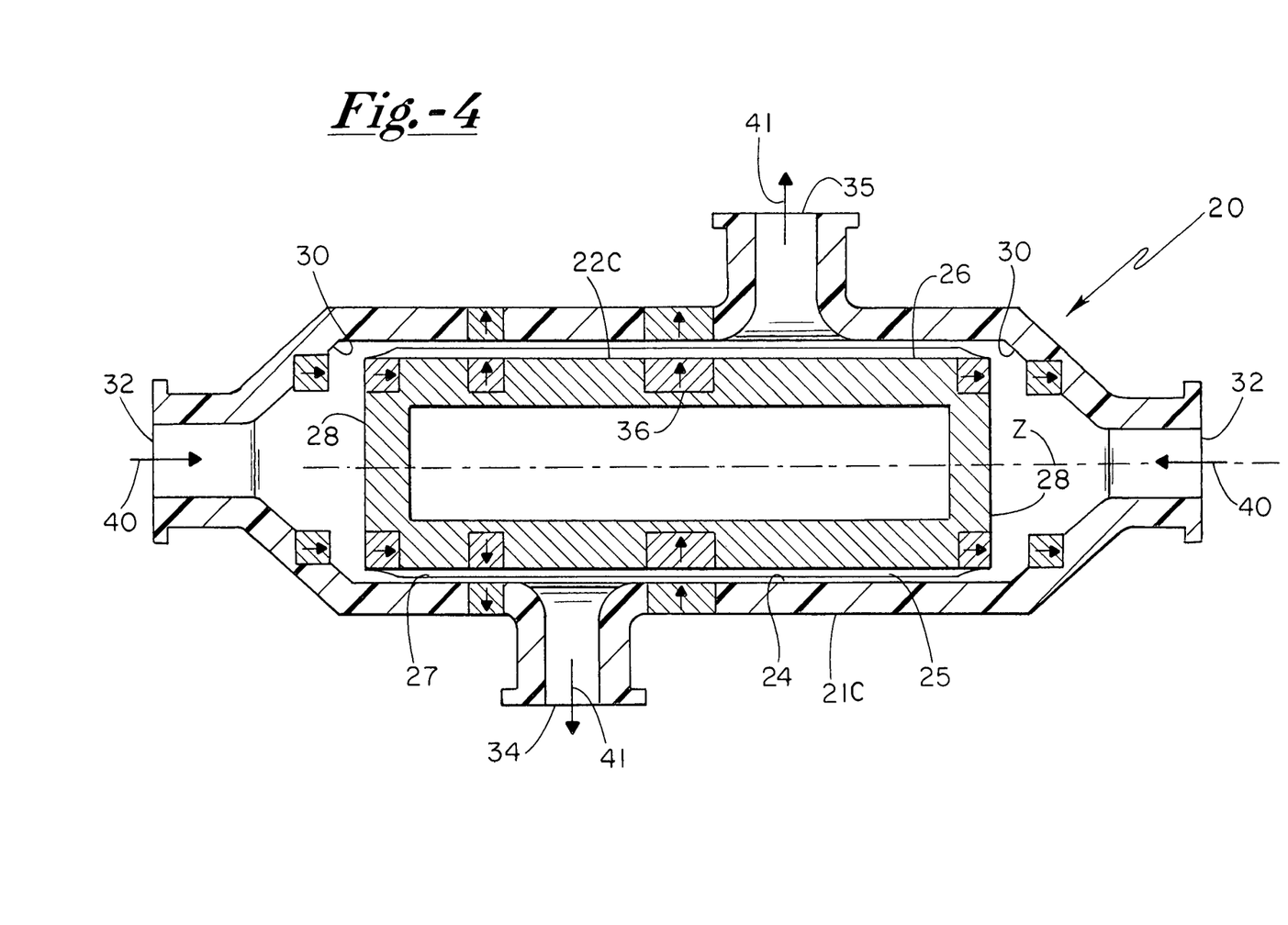
FIG. 4 is a view of a modified embodiment of the assembly of FIG. 1, and illustrating an arrangement of the present invention in a centrifugal fluid pump configuration.

With attention now being directed to FIG. 4 of the drawings, the modified embodiment illustrated therein is in a centrifugal fluid pump designated 20. Centrifugal fluid pump 20 comprises a shell or housing 21C along with a rotor structure 22C. Housing 21C has an inner wall 24 which defines a chamber zone 25 therewithin. Rotor 22C has an outer surface as at 26 which may, in certain applications, be provided with elongated radially extending fins (also referred to as vanes/blades) as at 27. The outer edges of fins 27 are spaced from wall 24 so as to define an annular gap or spacing therebetween. With rotor 22C having an outer surface as at 26, the chamber zone creates an annular opening. The end caps 28—28 of rotor 22C are closed, and spaced axially from inner ends 30—30 of housing or body 21C. Inlet ports such as provided at 32—32 along with a pair of symmetrically disposed outlet ports 34 and 35 may be provided for pump 20. Ports 34 and 35 are disposed an equal distance between the central transverse axis 36 of rotor 22C. Zones 25 and 28—28 are, of course, filled with the pumped media or fluid during operation, with the density of the media or fluid being greater than that of rotor 22C. During operation, the pumped fluid enters pump along the line and in the direction of the arrows 40—40, and exiting the line and in the direction of the arrows 41—41.

Figure 6:
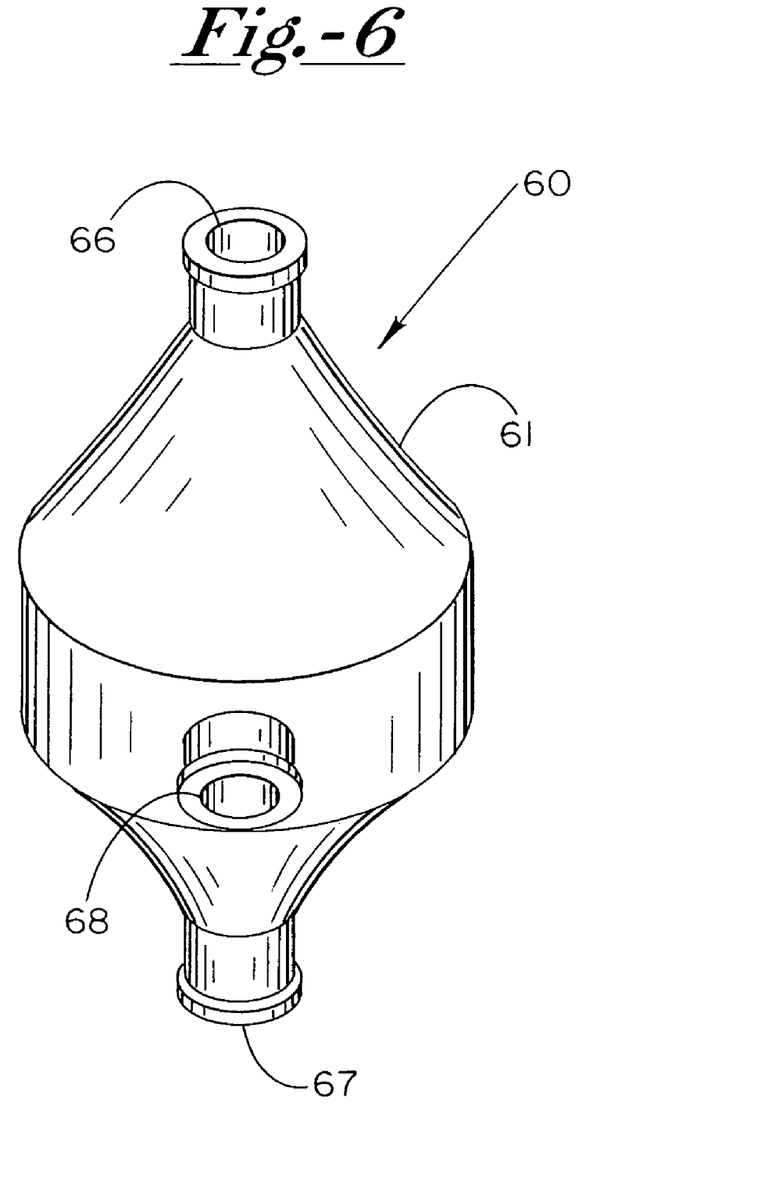
FIG. 6 is a perspective view of a fluid pump in accordance with the present invention.
Figure 7:
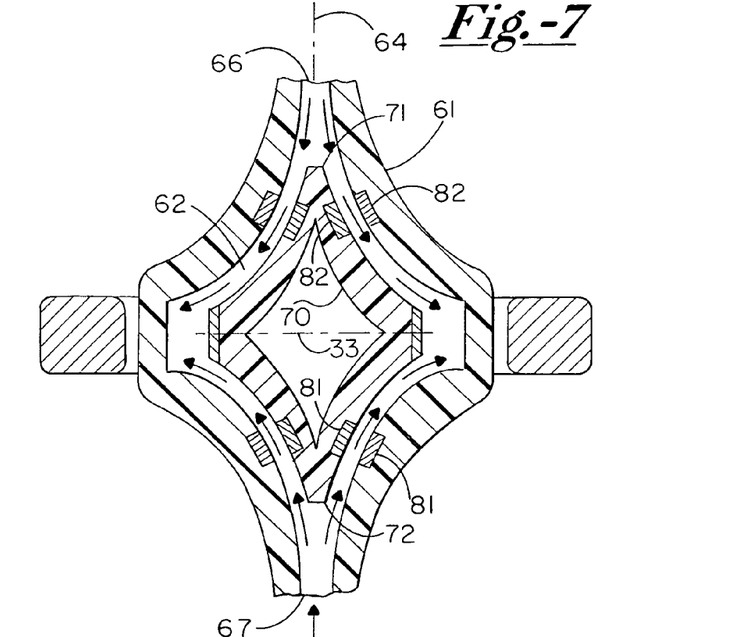
FIG. 7 is a cross-sectional view of the fluid pump assembly of FIG. 6.
Figure 8:
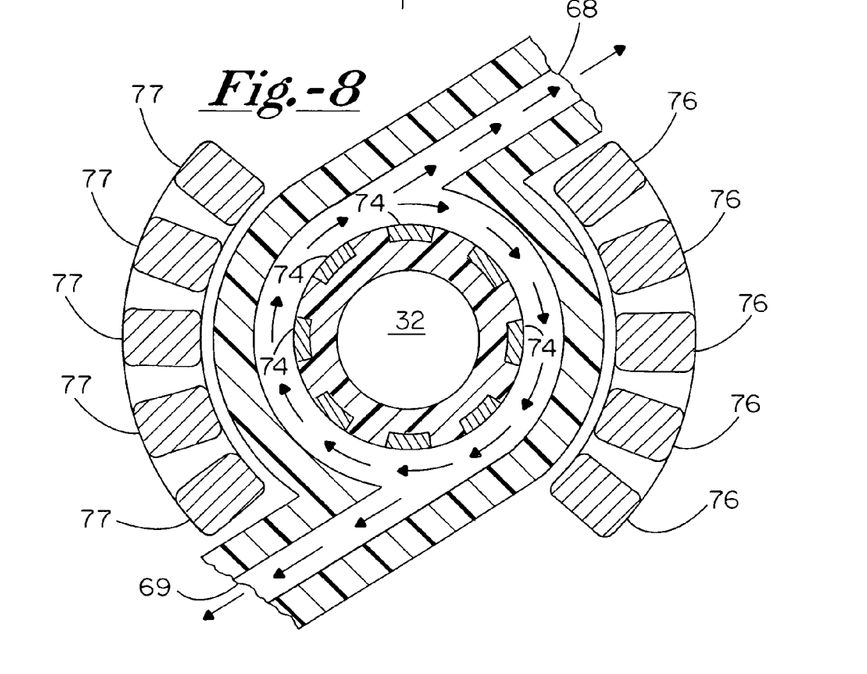
FIG. 8 is a top cross-sectional view of the fluid pump assembly of FIG. 6.

A preferred embodiment of the centrifugal fluid pump of the present invention is illustrated in FIG. 6, and is generally designated at 60. Centrifugal fluid pump 60 includes a housing 61, first and second inlet ports 66, 67, and first and second outlet ports 68, 69. As seen in FIGS. 7 and 8, the interior of housing 61 defines pumping chamber 62, such that housing 61 and chamber 62 share a central axis which extends along axis 64. Inlet ports 66 and 67 are preferably coaxially aligned with chamber 62 along axis 64, with inlet ports 66, 67 being arranged in oppositely disposed relationship to chamber 62. Outlet ports 68 and 69 are preferably arranged medially of inlet ports 66, 67, and are, as indicated, disposed generally transversely of axis 64.

Rotor 70 is disposed within chamber 62, and preferably has a symmetrical dual conical configuration. This configuration provides dual cones converging toward opposed polar regions such as 71, 72, and rotor 70 is provided with an axis of rotation which extends between polar regions 71, 72. The base of each of the two cones forming the dual cone configuration are coupled together and form a common center plane. This common center is preferably further utilized as a mounting base for a plurality of permanent drive magnets such as magnets 74—74. Preferably, drive magnets 74—74 are arranged at radially spaced locations generally medially along the axis of rotation of rotor 70, with the permanent drive magnets 74—74 being provided at equally radially and arcuately spaced locations. Electromagnetic drive means are provided as at 76—76 and 77—77, with the electromagnetic drive means being, in turn, coupled to a source of electrical energy and arranged to deliver rotational driving energy to rotor 70 through the permanent drive magnets 74—74. Such a drive arrangement is commonly referred to as a brushless motor configuration. The rate of rotation of rotor 70 is preferably controlled by means of the frequency of the field applied to electromagnetic members 76—76 and 77—77, with the rate of rotation being controlled by the frequency of the electromagnetic field, or by selective energization of the respective electromagnetic means 76—76 and 77—77.

As best depicted in FIG. 7, a plurality of passive magnetic bearings are provided, as at bearing sets 81—81 and 82—82. Passive bearing sets 81—81 and 82—82 may be in the form of an attractive bearing set, as illustrated in FIG. 3, or alternatively in a repulsive bearing set as in FIG. 5. The selection of the bearing set polarization is preferably dependent upon the desired configuration of pump housing 61 and rotor 70, as well as the relative placement of respective passive bearing sets 81—81 and 82—82. Such factors assist in determining a desired axis in which a negative stiffness characteristic created as a result of the Earnshaw principle is desirably aligned with respect to the axis of rotation 64 of rotor 70. The present invention contemplates a variety of configurations for pump 60 and rotor 70 as well as the placement and polarization of multiple passive bearing sets as at 81—81 and 82—82.

To assist in the passive and stable suspension of rotor 70 within housing 61, the density of rotor 70 is relatively lower than that of the fluid being pumped in pump 60. Such a low relative density of rotor 70 may preferably be achieved by providing rotor 70 as a hollow body. In addition, rotor 70 is preferably symmetrical in configuration, such that both the passive magnetic forces and centrifugal forces acting thereon cancel each other out when rotor 70 is positioned at a centrally-disposed origin of chamber 62.

In preferred embodiments of the present invention, pump 60 and, specifically, rotor 70 are preferably constructed of suitable bio-compatible materials such as polycarbonate, acrylic, or copolymers of polystyrene. Alternatively, a coating may be applied to a suitable substrate in order to enhance the biocompatibility of the structure. However, in applications wherein the device is not being employed for physiological implantation, other materials may be employed. Most preferably, however, housing 61 and rotor 70 are fabricated from materials consistent with the handling of fragile or aggressive fluids.

As indicated in FIGS. 7 and 8, fluid enters through inlets 66, 67 and is routed by rotor 70 to outlets 68, 69. The arrows depicted in FIGS. 7 and 8 illustrate the general flow direction of the fluid being pumped.

It will be appreciated, of course, that various modifications may be made in the preferred embodiment illustrated above, and these modifications may be made without actually departing from the spirit and scope of the present invention.

What is claimed is:

1. A fluid pump comprising:
  (a) a housing with an inner wall defining a chamber having an axis and having opposed ends disposed coaxially with said chamber;
  (b) a rotor having opposed first and second ends and being operationally disposed within said chamber and having a rotor axis defining an axis of rotation, said rotor comprising:
    (i) a rotor body having a relative density substantially less than that of the respective fluid being pumped;
    (ii) a configuration defining a surface of revolution with an axial length defined between said first and second ends and providing a predetermined clearance between said rotor and said first and second ends, and with a diameter of said rotor body transverse to said axis of rotation being selected to provide a predetermined radial clearance between an outer surface of said rotor body and the inner wall of said housing, the clearances between said rotor and said housing being sufficiently large so as to render the effects of hydrodynamic bearings ineffective in stably supporting said rotor;
  (c) drive magnets disposed on said rotor and being positioned radially outwardly of said rotor axis generally medially of said first and second ends;
  (d) an electromagnetic drive mechanism coupled to a source of energy and arranged along said housing to deliver rotational driving energy to said rotor through said drive magnets; and
  (e) a plurality of passive magnetic bearing sets disposed on said housing and said rotor, said passive magnetic bearing sets including first and second magnetic bodies in mutually magnetically coupled relationship, with the first magnetic bodies of each bearing set being mounted on said rotor and with the second magnetic bodies of each bearing set being mounted along the inner wall of said housing, said first magnetic bodies being disposed adjacent to and in magnetically coupled relationship to respective second magnetic bodies to form respective bearing sets, each of said first and second magnetic bodies solely comprising a permanent magnet, each of the said first and second magnetic bodies comprising each of said passive magnetic bearing sets being polarized and positioned in mutually attracting or mutually repelling relationship so as to function as bearings selected from the group consisting of radial and thrust, said plurality of passive magnetic bearing sets being further arranged to form a passive suspension for said rotor within said housing, with said passive suspension having negative stiffness only in directions perpendicular to the rotor axis of rotation, such negative stiffness being of a magnitude such that centrifugal forces developed during rotation of said rotor overcome said negative stiffness and create positive stiffness of said rotor suspension in all required degrees of freedom.

2. The fluid pump of claim 1 wherein said housing has an inlet port at one end of said housing and in substantial coaxial relationship with said chamber axis, and an outlet port disposed on the wall of said housing generally medially of said chamber axis.

3. The fluid pump of claim 2 wherein the outer surface of said rotor body has a plurality of radially extending vanes.

4. The fluid pump of claim 1 wherein said housing includes an inlet port and an outlet port oppositely disposed at respective opposed ends thereof in coaxial relationship with said chamber axis.

5. The fluid pump of claim 2, including one or more spaced apart disks radially disposed about said chamber axis and integrally coupled to said rotor for assisting in pumping the fluid through said pump.

6. The fluid pump of claim 1 wherein selected of said second magnetic bodies of at least one passive magnetic bearing set are operationally disposed in spaced apart relationship from said housing.

7. The fluid pump of claim 1, including at least one passive electrostatic bearing set.

* * * * *